United States Patent
Darian

(12) 
(10) Patent No.: US 10,398,465 B2
(45) Date of Patent: Sep. 3, 2019

(54) ULTRASONIC SURGICAL INSTRUMENT ASSEMBLY, RELATED ACCESSORY, AND ASSOCIATED SURGICAL METHOD

(71) Applicant: MISONIX, INCORPORATED, Farmingdale, NY (US)

(72) Inventor: Alexander Darian, Brightwaters, NY (US)

(73) Assignee: MISONIX INCORPORATED, Farmingdale, NY (US)

( * ) Notice: Subject to any disclaimer, the term of this patent is extended or adjusted under 35 U.S.C. 154(b) by 0 days.

(21) Appl. No.: 14/264,705

(22) Filed: Apr. 29, 2014

(65) Prior Publication Data

US 2015/0306428 A1    Oct. 29, 2015

(51) Int. Cl.
| A61B 17/00 | (2006.01) |
| A61B 17/32 | (2006.01) |
| A61B 18/00 | (2006.01) |
| A61B 90/30 | (2016.01) |

(52) U.S. Cl.
CPC ...... *A61B 17/320068* (2013.01); *A61B 90/30* (2016.02); *A61B 2017/00477* (2013.01); *A61B 2018/00178* (2013.01); *A61B 2090/309* (2016.02)

(58) Field of Classification Search
CPC .............................. A61N 7/00; A61H 23/0245
See application file for complete search history.

(56) References Cited

U.S. PATENT DOCUMENTS

| 4,223,676 A | | 9/1980 | Wuchinich et al. |
| 4,526,177 A | * | 7/1985 | Rudy ........................ A61B 5/06 324/236 |
| 4,683,873 A | * | 8/1987 | Cadossi ................... A61N 2/02 600/14 |
| 4,979,952 A | | 12/1990 | Kubota et al. |
| 5,176,677 A | * | 1/1993 | Wuchinich ................ A61F 2/46 604/22 |
| 5,188,102 A | | 2/1993 | Idemoto et al. |
| 5,361,503 A | * | 11/1994 | Anderson ................ G01C 9/32 33/348.2 |
| 5,469,067 A | * | 11/1995 | Endoh ................... G01R 31/021 324/541 |
| 5,527,273 A | | 6/1996 | Manna et al. |
| 6,379,296 B1 | * | 4/2002 | Baggett .................. A61B 1/303 600/178 |
| 6,379,371 B1 | | 4/2002 | Novak et al. |
| 6,386,866 B1 | | 5/2002 | Hecht et al. |
| 7,931,611 B2 | | 4/2011 | Novak et al. |

(Continued)

FOREIGN PATENT DOCUMENTS

| CN | 103675407 A | 3/2014 |
| DE | 3706934 A1 | 9/1988 |

*Primary Examiner* — Hien N Nguyen
(74) *Attorney, Agent, or Firm* — R. Neil Sudol; Henry D. Coleman

(57) ABSTRACT

An ultrasonic surgical instrument assembly includes a handpiece, a generator of ultrasonic mechanical vibrations disposed in the handpiece, a probe, and a light source. The probe is attached to a distal end of the handpiece and is operatively connected to the generator. The light source is removably attached to the handpiece and is configured and mounted to direct at least visible electromagnetic radiation in a direction along the probe so as to illuminate a surgical site distal of the probe.

5 Claims, 1 Drawing Sheet

(56) References Cited

U.S. PATENT DOCUMENTS

| | | | |
|---|---|---|---|
| 2004/0223321 A1* | 11/2004 | Crowley | F21L 4/06 362/103 |
| 2006/0025836 A1* | 2/2006 | Van Gerpen | A61H 3/00 607/88 |
| 2007/0166663 A1* | 7/2007 | Telles | A61C 17/20 433/119 |
| 2008/0064006 A1 | 3/2008 | Quan et al. | |
| 2012/0116265 A1* | 5/2012 | Houser | A61B 17/00234 601/2 |
| 2013/0303845 A1 | 11/2013 | Skula et al. | |
| 2014/0207002 A1* | 7/2014 | Seow | A61B 8/4416 600/459 |

\* cited by examiner

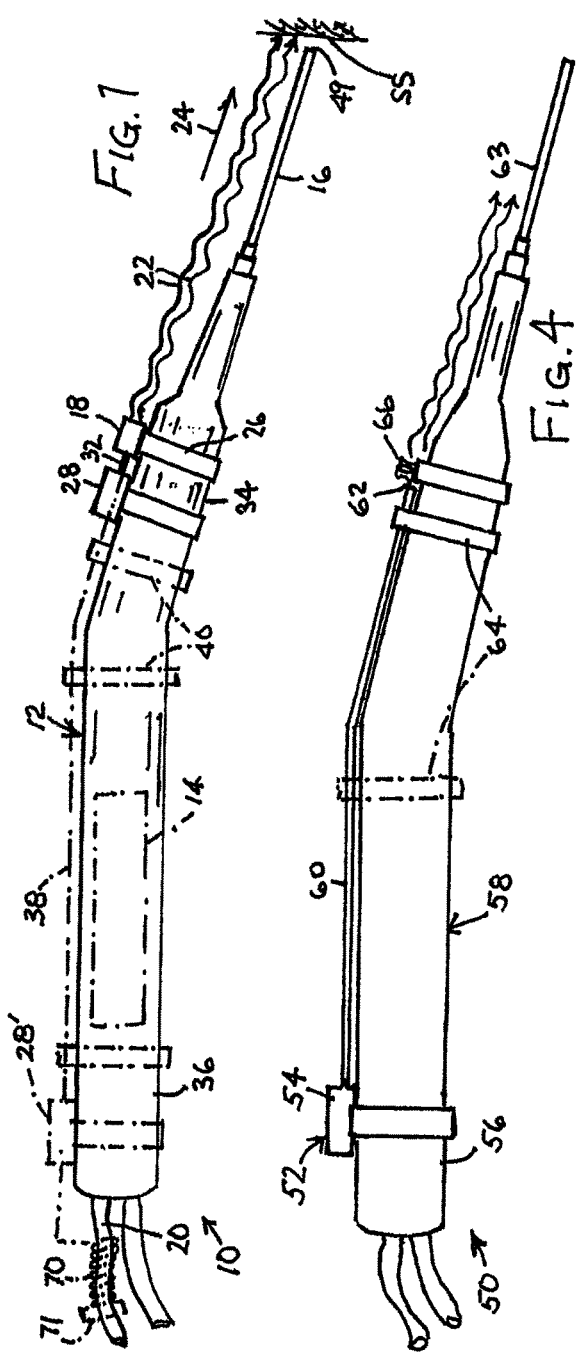
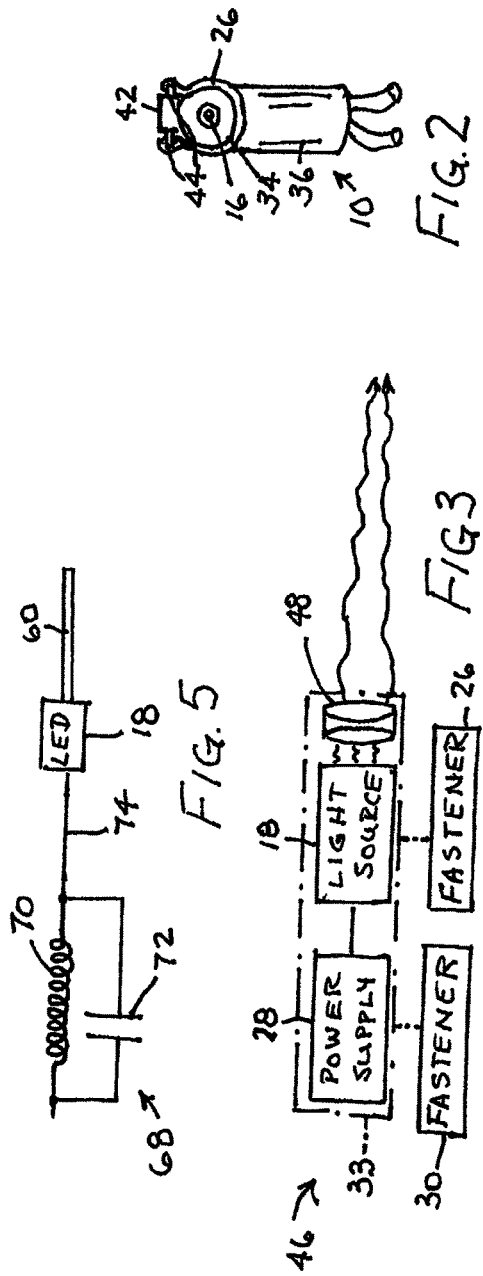

ULTRASONIC SURGICAL INSTRUMENT ASSEMBLY, RELATED ACCESSORY, AND ASSOCIATED SURGICAL METHOD

BACKGROUND OF THE INVENTION

This invention relates to an ultrasonic surgical instrument assembly. This invention also pertains to an accessory for use with an ultrasonic surgical instrument. This invention additionally related to an associated surgical method.

Over the past 30 years, several ultrasonic tools have been invented which can be used to ablate or cut tissue in surgery. Wuchinich et al. in U.S. Pat. No. 4,223,676 and Idemoto et al in U.S. Pat. No. 5,188,102 disclose such devices.

Ultrasonic surgical devices generally fall into two categories. One is a blunt tip hollow probe that vibrates at frequencies between 20 kc and 100 kc, with amplitudes up to 300 microns or more. Such devices ablate tissue by either producing cavitation bubbles which implode and disrupt cells, tissue compression and relaxation stresses (sometimes called the jackhammer effect) or by other forces such as microstreaming of bubbles in the tissue matrix. The effect is that the tissue becomes liquefied and separated. It then becomes emulsified with the irrigant solution. The resulting emulsion is then aspirated from the site. Bulk excision of tissue is possible by applying the energy around and under unwanted tumors to separate it from the surrounding structure. The surgeon can then lift the tissue out using common tools such as forceps.

A second kind of ultrasonic device uses a sharp blade instead of a blunt hollow probe. Here a cutting action takes place. Such a sharp ultrasonic blade is the subject of allowed U.S. Pat. No. 6,379,371. As disclosed therein, the blade shape is semicircular at the distal portion with two straight sides parallel to the longitudinal axis and extending back to the shoulder that contacts the vibrating probe. Male threads are shown which mate with the female threaded socket of the probe (or transducer) to allow tight intimate contact of the probe and blade tip shoulder. When the two are torqued together, they form a single resonant body that will vibrate in sympathy with the transducer and generator combination. The distal end of the blade will vibrate with an amplitude set by the mechanical gain of the probe/tip geometry and the input amplitude provided by the transducer generator combination. This motion provided the cutting action for the tissue in question.

The blade of U.S. Pat. No. 6,379,371 was intended for the cutting or excising of bone or similarly hard tissue in surgical applications. In tests conducted in vitro and in vivo, it was noted that the blade, when sharp, cut both hard and soft tissue with similar ease. In delicate operations, such as sinus lift surgery or craniotomies where the goal is to cut an aperture in the front of the skull to expose sinus tissue or brain but not cut the membrane directly beneath the bony structure, this is very important. It is also important in spinal and brain surgery where bone tissue must be cut with a minimum of damage to underlying soft tissues such as the dura mater. It was noted in early in vitro testing that the blade, as it plunged through the cortex of the bone punctured the membrane or ripped it. After some experience, competent surgeons were able to master the technique, but the learning curve was steep.

A sharp blade such as that of U.S. Pat. No. 6,379,371 has been shown in both in vitro and in vivo testing to be an effective tool for cutting bone, cartilage, soft tissues such as vein, arteries and can even be used to cut skin with minimal secondary trauma. In this kind of blade, ablation is not the primary cause but a shearing or cutting action predominates.

Ultrasonic surgical tools as described above are more effective than conventional surgical instruments in ablating certain kinds of tissue. However, this very effectiveness can result in unwanted damage to organic tissues, for instance, when operating conditions are such that a sufficient degree of care cannot be properly exercised. This may happen, for instance, when the surgical site is not properly illuminated.

OBJECTS OF THE INVENTION

It is an object of the present invention to provide an improved medical instrument assembly, particularly including ultrasonic surgical instrument assemblies.

It is a more specific object of the present invention to provide such an instrument assembly which facilitates an enhanced degree of care and attention in carrying out medical, e.g., ultrasonic surgical, procedures.

It is an even more particular object of the present invention to provide such an instrument assembly that facilitates perception of tissues at a surgical site.

A related object of the present invention is to provide an accessory utilizable with a medical instrument that facilitates visualization of tissues at a target tissue site.

A more specific object of the present invention is to provide a surgical method using an ultrasonic surgical instrument, wherein visualization of tissues at a surgical site is enhanced or facilitated.

An even more specific object of the present invention is to provide a medical instrument assembly and/or associated medical method wherein the meeting of power supply requirements is facilitated.

These and other objects of the invention will be apparent to those skilled in the art from the drawings and descriptions hereof. Although each object is attained by at least one embodiment of the invention, no embodiment need necessarily meet every object.

SUMMARY OF THE INVENTION

An ultrasonic surgical instrument assembly in accordance with the present invention comprises a handpiece, a transducer generating ultrasonic mechanical vibrations and disposed in the handpiece, a probe, and a light source. The probe is attached to a distal end of the handpiece and is operatively connected to the transducer or vibration generator. The light source is attached to the handpiece and is configured and mounted to direct at least visible electromagnetic radiation in a direction along the probe so as to illuminate a surgical site distal of the probe.

It is contemplated that the instrument assembly additionally comprises a power supply component. The power supply component may take the form of a power cord (optionally with an AC-to-DC adapter) extendable to an electrical wall outlet. Preferably, however, the power supply component is a dedicated piece attachable directly to the handpiece or indirectly, e.g., via a power transmission cord or cable extending to the transducer or vibration generator.

Pursuant to a specific feature of the present invention, the power supply includes a coil which is disposed about a power cable feeding the transducer or vibration generator. The power supply may further include a slow-drain capacitor for providing energy or power to the light source for a predetermined period of time after termination of power conduction through the cable.

Typically, the light source is removably attached to the handpiece via a fastener such as a clip, clamp, band, strap, ring, or hook and loop fasteners. At least one additional fastener may be provided for removably attaching the power supply at least indirectly to the handpiece.

The power supply typically includes a battery, while the light source may comprise a light-emitting diode. The light source may be attached to a distal end of the handpiece and oriented to provide illumination along the probe to a surgical site. Alternatively, the light source may be attached to a proximal or rear end of the handpiece, in which case the instrument assembly further comprises an optical fiber extending from the light source to a distal end portion of the handpiece. A free or outlet end of the optical fiber is arranged to point distally, i.e., in a direction along the probe so as to illuminate a surgical site distal of the probe.

The present invention is concomitantly directed to an accessory for a surgical instrument which includes a handpiece, an ultrasonic vibration transducer disposed in the handpiece, and a probe attached to a distal end of the handpiece, where the probe is operatively connected to the transducer. The accessory comprises (a) a light source, (b) a fastener for removably attaching the light source to the handpiece, and, optionally, (c) a power supply component operatively connectable to the light source. Optionally, the power supply component is mountable at least indirectly to the handpiece. In the case of a cable or electrical cord, the power supply may be connected only indirectly to the handpiece via the light source.

The power supply may include a coil disposable about a power cable feeding the transducer or vibration generator. An additional fastener is provided for removably attaching the coil about the power cable. As indicated above, the power supply may further include a slow-drain capacitor operatively connected to the coil and connectable to the light source for providing illumination energy to the light source for a predetermined period of time after a termination of power conduction through the cable.

Where the fastener is configured for attaching the light source to a proximal or rear end of the handpiece, the accessory further comprises an optical fiber and at least one additional fastener for removably attaching the optical fiber to the handpiece so that the optical fiber extends from the light source to a distal end portion of the handpiece.

A surgical method comprises, in accordance with the present invention, (i) providing a surgical instrument having a handpiece, a transducer or generator of ultrasonic mechanical vibrations disposed in the handpiece and a probe attached to a distal end of the handpiece and operatively connected to the transducer or vibration generator. The method also comprises (ii) providing a light source, (iii) applying a fastener to handpiece to attach the light source thereto so that light from the light source is directable generally parallel to the probe, (iv) operating the surgical instrument to apply ultrasonic vibratory energy to a surgical site, (v) conducting electrical energy from a power supply to the light source during the operating of the surgical instrument, and (vi) illuminating the surgical site with light from the source during the operating of the surgical instrument and the conducting of the electrical energy.

Pursuant to another feature of the present invention, the surgical method further comprises removably mounting the power supply at least indirectly to the handpiece. Where the power supply includes a coil, the removable mounting of the power supply at least indirectly to the handpiece includes disposing the coil about a power cable feeding the transducer or vibration generator. Where the power supply further includes a slow-drain capacitor operatively connected to the coil, the surgical method further comprises operating the capacitor to provide illumination energy to the light source for a predetermined period of time after a termination of power conduction through the cable.

It is contemplated that the method further comprises removing the fastener and the light source from the handpiece after completion of an operation on the surgical site. The fastener, the light source, the power supply may be disposable components.

Pursuant to another feature of the present invention, the applying of the fastener includes positioning the light source at a proximal or rear end of the handpiece. In that case, the surgical method further comprises attaching an optical fiber to the handpiece so that the fiber extends from the light source at the proximal end of the handpiece to a distal end of the handpiece.

BRIEF DESCRIPTION OF THE DRAWINGS

FIG. 1 is a schematic side elevational view of an ultrasonic instrument assembly in accordance with the present invention.

FIG. 2 is a schematic front elevational view of the ultrasonic instrument assembly of FIG. 1.

FIG. 3 is a block diagram of an accessory for an ultrasonic instrument, in accordance with the present invention.

FIG. 4 is a schematic side elevational view of another ultrasonic instrument assembly in accordance with the present invention.

FIG. 5 is a circuit diagram showing a modification of the accessory of FIG. 3.

DETAILED DESCRIPTION

As shown in FIGS. 1 and 2, an ultrasonic surgical instrument assembly 10 comprises a handpiece 12, a generator 14 of ultrasonic mechanical vibrations, a probe 16, and a light source 18. Generator 14 is encased in handpiece 12 and typically takes the form of an electromechanical transducer such as a piezoelectric crystal stack. Generator is energized by an alternating electrical waveform of ultrasonic frequency carried by a power transmission cord or cable 20 extending to the generator via a rear or proximal end 36 of the handpiece.

Probe 16 is shown as a tubular member but may take any form conducive to the applications of ultrasonic mechanical vibrations to organic tissues. Thus, probe 16 may exemplarily take the form of a planar cutting blade as disclosed in U.S. Pat. No. 6,379,371, a lipectomy probe as disclosed in U.S. Pat. No. 5,527,273, or a debrider tool as disclosed in U.S. Pat. No. 7,931,611. Probe 16 is attached to a distal end of handpiece 12 and is operatively connected to generator 14. Light source 18 is attached to handpiece 12 and is configured and mounted to direct visible electromagnetic radiation 22 in a direction 24 along probe 16 so as to illuminate a surgical site SS distal of the probe Light source 18 preferably includes one or more light emitting diodes (LEDs) and is removably attached to handpiece 12 via a fastener 26, which is depicted as a band or strap but may take any other suitable form such as a clip, clamp, ring, snap fastener, hook and eyelet fastener, or hook and loop fastener.

Instrument assembly 10 additionally comprises a power supply component 28 in the form of a battery or other dedicated piece attachable directly to handpiece 12 via an additional fastener 30 such as a band, strap, clip, clamp, ring, snap fastener, hook and eyelet fastener, or hook and loop fastener. Light source 18 and power supply component 28 are shown spaced from one another and interconnected by at least one wire 32. Alternatively, light source 18 and power supply component 28 may be provided in a common housing or casing 33.

FIG. 1 shows power supply component 28 as attached to a distal end portion 34 of handpiece 12, near light source 18. However, power supply component 28 may be alternatively attached to proximal end 36 of handpiece 12, as indicated at 28'. At least one wire or lead 38 extends from power supply component 28' to light source 18. Auxiliary bands or straps 40 may be provided for maintaining wire or lead 38 in place along handpiece 12, thereby minimizing interference with manipulations of the handpiece during a surgical procedure.

FIG. 2 shows light source 18 as having a casing or housing 42 provided with a pair of eyelet elements 44 to which band or strap fastener 26 is coupled.

FIG. 3 diagrammatically illustrates an accessory 46 for retro-fitting a surgical instrument (e.g., handpiece 12, generator 14, probe 16) to illuminate a surgical site SS (FIG. 1). Light source 18 may include a lens or composite lens 48 for focusing the emitted radiation at a point immediately ahead of a distal tip 49 of probe 16 (FIG. 1), thereby enhancing the effective illumination of surgical site SS.

As depicted in FIG. 4, a light source 52 for an ultrasonic surgical instrument 50 includes an LED component 54 attachable to the proximal or rear end 56 of a casing or housing 58. Light source 52 further includes an optical fiber or fiber bundle 60 that extends from LED component 54 in a longitudinal direction along casing or housing 58. The optical fiber or fiber bundle 60 terminates in a distal tip 62 that serves as an illumination port arranged to point distally, i.e., in a direction along a probe 63 so as to illuminate a surgical site distal of the probe. Optical fiber or bundle 60 is attached to casing or housing 58 via multiple fasteners 64 each taking any suitable form including but not limited to a band, strap, clip, clamp, ring, snap fastener, hook and eyelet fastener, or hook and loop fastener. Light source 52 may additionally include a lens or lens assembly 66.

An alternative form of power supply 68 for energizing a light source as described herein is illustrated in FIG. 5. Power supply 68 particularly includes an inductance coil 70. Coil 70 may be attached via a clip or other fastener 71 about power cord or cable 20 (FIG. 1) and connected to light source 18. Coil 70 inductively generates a waveform at the same frequency as the signal transmitted through power cord 20. Power supply 68 may further include a slow-drain capacitor 72 connected in parallel to inductance coil 70 for providing energy or power to the light source 18 for a predetermined period of time after termination of power conduction through cord or cable 20. An electrical wire 74 (generally a pair of leads) extends from coil 70 and optionally capacitor 72 to light source 18 and may be attached to the handpiece 12 of the instrument 10 via fasteners as discussed above. Power supply 68 is considered particularly advantageous in the drawing of power from the power cord of cable 20, thereby obviating an additional line extending to the handpiece from a distant electrical outlet or the use of a battery.

A surgical method utilizing the instrument 10 of FIG. 1 entails providing light source 18 and applying at least one fastener 26 to handpiece 12 to attach the light source thereto in such a manner that light from the light source is directable generally parallel to the probe 16 (arrow 24). Surgical instrument 10 is then operated to apply ultrasonic vibratory energy to surgical site SS, electrical energy being conducted from power supply 28 to light source 18 during the operating of the surgical instrument. Surgical site SS is illuminated with light from source 18 during the operating of the surgical instrument 10 and the conducting of the electrical energy.

It is contemplated that the power supply 28 is removably mounted at least indirectly to handpiece 12. Where the power supply 28 or 68 includes coil 70, the removable mounting of the power supply at least indirectly to handpiece 12 includes disposing the coil about power cable 20. Where the power supply 28 or 68 further includes slow-drain capacitor 72 operatively connected to coil 70, the surgical method further comprises operating the capacitor to provide electrical energy to light source 18 or 52 for a predetermined period of time after a termination of power conduction through the cable 20.

It is contemplated that the method further comprises removing all illumination accessories including fastener 26, power supply 28, and light source 18 from handpiece 12 after completion of an operation on surgical site SS. Fastener 26, light source 18, and power supply 28 may be disposable components.

A similar procedure applies to other embodiments of the invention described above with reference to FIGS. 3-5.

Although the invention has been described in terms of particular embodiments and applications, one of ordinary skill in the art, in light of this teaching, can generate additional embodiments and modifications without departing from the spirit of or exceeding the scope of the claimed invention. For example, light source 18 may be designed to emit electromagnetic radiation having wavelength wholly or partially outside of the visible range. Ultraviolet radiation may be used where organs have been exposed to fluorescent compounds. Infrared radiation might be used to increase local tissue temperatures at a surgical site, for instance, to enhance visualization via infrared imaging lenses or cameras.

Although the present invention is directed particularly to ultrasonic surgical instruments, the light source accessory could also be used with other kinds of medical instrumentation, including diagnostic tools and conventional surgical instruments. A medical instrument assembly in accordance with the present invention comprises an instrument with a handpiece and a light source attached to the instrument (either the handpiece or a tool extension or accessory thereof) and so mounted and configured to direct at least visible electromagnetic radiation in a direction along a distal end portion of the instrument so as to illuminate a target tissue site distal of the distal end portion of the instrument.

The power supply component may take the form of a power cord (optionally with an AC-to-DC adapter) extendable to an electrical wall outlet.

Accordingly, it is to be understood that the drawings and descriptions herein are proffered by way of example to facilitate comprehension of the invention and should not be construed to limit the scope thereof.

What is claimed is:

1. An ultrasonic surgical instrument assembly comprising:
   a handpiece;
   a transducer or generator of ultrasonic mechanical vibrations disposed in said handpiece;
   a power cable extending to said handpiece and operatively connected to said transducer or generator for conducting electrical energy thereto;
   a probe attached to a distal end of said handpiece and operatively connected to said transducer or generator;

a light source attached to said handpiece so as to direct at least visible electromagnetic radiation along the probe towards a surgical site distal of the probe;

a power supply mounted at least indirectly to said handpiece and operatively connected to said light source, said power supply including a coil wrapped around said power cable outside of said handpiece for inductively generating a waveform at a same frequency as a signal transmitted through said power cable; and a fastener for removably attaching said light source to said handpiece, said power supply further including a capacitor for providing energy or power to said light source for a predetermined period of time after termination of power conduction through said cable.

2. The surgical instrument assembly defined in claim 1, further comprising at least one additional fastener for removably attaching said power supply at least indirectly to said handpiece.

3. The surgical instrument assembly defined in claim 1 wherein said light source includes a light-emitting diode.

4. The surgical instrument assembly defined in claim 1 wherein said light source is attached to a proximal or rear end of said handpiece, further comprising an optical fiber extending from said light source to a distal end portion of said handpiece.

5. The surgical instrument assembly defined in claim 1 wherein said light source is attached to a distal end of said handpiece and is oriented to provide illumination along said probe to the surgical site.

\* \* \* \* \*